US006945116B2

(12) United States Patent
Xie et al.

(10) Patent No.: US 6,945,116 B2
(45) Date of Patent: Sep. 20, 2005

(54) INTEGRATED CAPACITIVE MICROFLUIDIC SENSORS METHOD AND APPARATUS

(75) Inventors: Jun Xie, Pasadena, CA (US); Jason Shih, Yorba Linda, CA (US); Yu-Chong Tai, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/802,667

(22) Filed: Mar. 16, 2004

(65) Prior Publication Data

US 2004/0237657 A1 Dec. 2, 2004

Related U.S. Application Data

(60) Provisional application No. 60/456,019, filed on Mar. 19, 2003.

(51) Int. Cl.[7] .................................................. G01L 9/12
(52) U.S. Cl. ........................................................ 73/724
(58) Field of Search ........................... 73/700, 718, 724

(56) References Cited

U.S. PATENT DOCUMENTS 5,625,139 A * 4/1997 Stormbom .................. 73/23.21
6,809,462 B2 * 10/2004 Pelrine et al. .............. 310/319

OTHER PUBLICATIONS

J. Xie, J. Shih, Y.C. Tai. (2003). "Integrated Surface–Micromachined Mass Flow Controller." 16th IEEE International Conference on Micro Electro Mechanical Systems (MEMS '03). p. 443–448.
J. Xie, Q. He, Y.C. Tai, J. Liu, T. Lee. (2003). "Electrolysis–Based On–Chip Dispensing System For ESI–MS." IEEE International Conference on Micro Electro Mechanical Systems (MEMS '03). p. 443–446.
J. Xie, X. Yang, X.Q. Wang, Y.C. Tai, (2001). "Surface Micromachined Leakage Proof Parylene Check Valve." 14th IEEE International Conference on Micro Electro Mechanical Systems (MEMS '01), p. 539–542.
K. Shida, A.B.M. Ismail, (1999). "Measurement of Concentration of Electrolytic Solution Based on Novel Non–Contact Multi–Sensing Techniques." IEEE Instrumentation and Measurement Technology Conference, (IMTC'99), p. 1372–1376.
R.E. Oosterbroek, T.S.J. Lammerink, J.W. Berenschot, A. van den Berg, Elwenspoek. (1997). "Designing, Realization And Characterization Of A Novel Capactive Pressure/Flow Sensor," International Conference on Solid–State Sensors and Actuators (Transducers '97). p. 151–154.
S. Wu, J. Mai, Y.Zohar, Y.C, Tai, C.M. Ho. (1998). "A Suspended microchannel with Integrated Temperature Sensors for High–Pressure Flow Studies." 11th IEEE International Workshop on Micro Electro Mechanical Systems (MEMS '98). p. 87–92.
T.J. Yao, X. Yang, Y.C. Tai. (2001). "BrF$_3$ Dry Release Technologies for Large Freestanding Parylene MEMS," International Conference on Solid–State Sensors and Actuators (Transducers '01). p. 652–655.

* cited by examiner

Primary Examiner—Max Noori
(74) Attorney, Agent, or Firm—Foley & Lardner LLP

(57) ABSTRACT

A microfluidic device and method for capacitive sensing. The device includes a fluid channel including an inlet at a first end and an outlet at a second end, a cavity region coupled to the fluid channel, and a polymer based membrane coupled between the fluid channel and the cavity region. Additionally, the device includes a first capacitor electrode coupled to the membrane, a second capacitor electrode coupled to the cavity region and physically separated from the first capacitor electrode by at least the cavity region, and an electrical power source coupled between the first capacitor electrode and the second capacitor electrode and causing an electric field at least within the cavity region. The polymer based membrane includes a polymer.

25 Claims, 16 Drawing Sheets

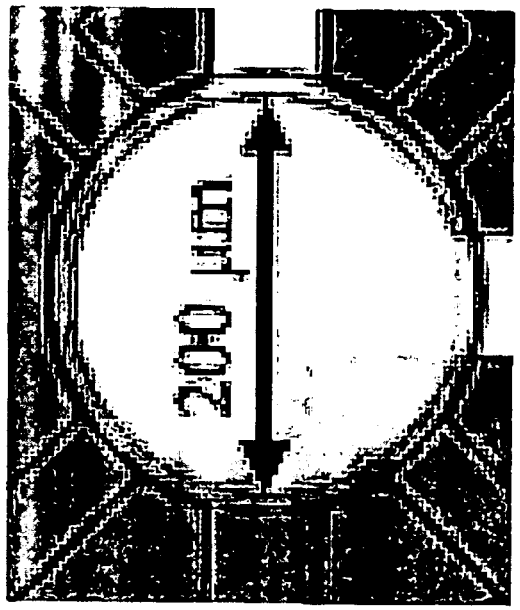
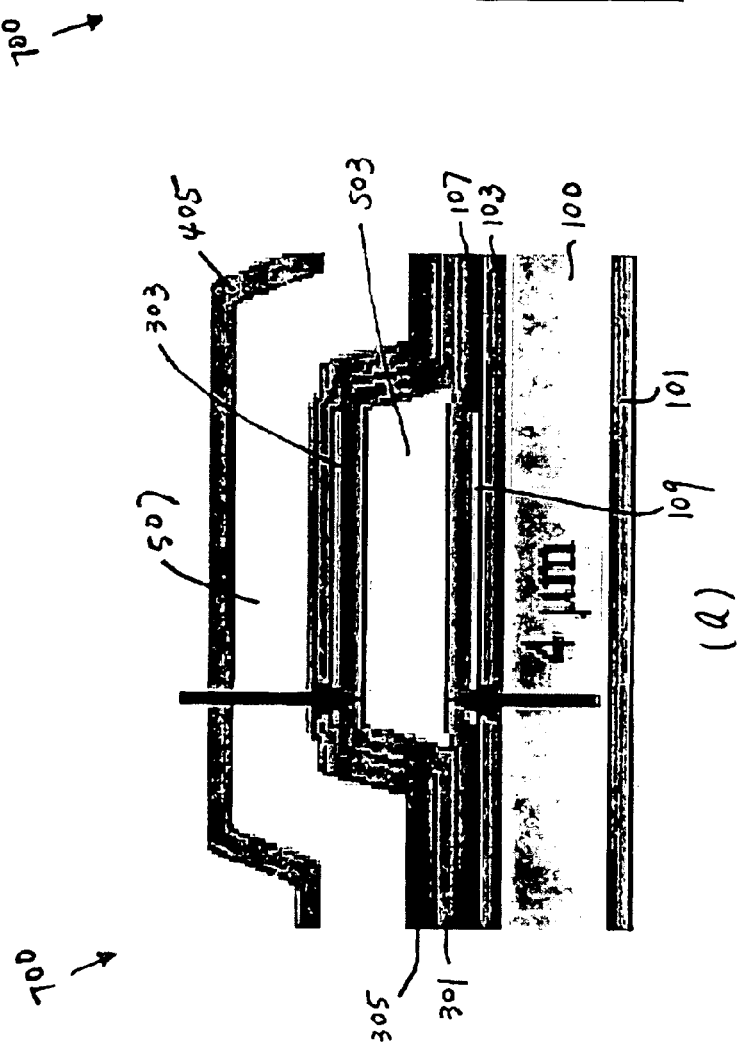
Fig 7

INTEGRATED CAPACITIVE MICROFLUIDIC SENSORS METHOD AND APPARATUS

CROSS-REFERENCES TO RELATED APPLICATIONS

This application claims priority to U.S. Provisional patent application No. 60/456,019 filed Mar. 19, 2003, commonly assigned, incorporated by reference herein for all purposes.

STATEMENT AS TO RIGHTS TO INVENTIONS MADE UNDER FEDERALLY SPONSORED RESEARCH OR DEVELOPMENT

Work described herein has been supported, in part, by DARPA/MTO Bioflips Program (Grant No. N66001-00-C-8092), National Institute of Health (Grant No. 5R01RR06217-10), NSF CNSE Engineering Research Center at Caltech (Grant No. EEC-9402726). The United States Government may therefore have certain rights in the invention.

BACKGROUND OF THE INVENTION

The present invention relates generally to micro fabrication techniques. More particularly, the invention provides a method and device for manufacturing a fluidic sensing device using a micromachining method and apparatus. Merely by way of example, the invention has been applied to the manufacture of a polymer based capacitive fluidic sensing device. But it would be recognized that the invention has a much broader range of applicability. For example, the invention can be applied to other applications.

A Micro-Electro-Mechanical System, commonly called MEMS, is generally a batch-fabricated (micro fabricated) system that includes both electrical and mechanical elements. MEMS elements often have characteristic sizes ranging from nanometers to millimeters. MEMS often makes possible certain systems that are smaller, faster, more economical, and energy efficient in some cases. In a general MEMS system, the electrical portion includes integrated circuits, which forms the thinking part, while the electro-mechanical portion works with the thinking part to control functions and perception.

MEMS generally includes micro sensors and actuator devices. Micro sensors often gather outside information such as thermal, biological, optical, gravitational, and others. Actuators often respond to user based information to control their environment. As merely an example, capacitive sensing devices are common examples of MEMS. Capacitive sensors have been applied to microfluidic applications in the form of pressure sensors and flow sensors based on a differential pressure principle. Also, capacitive sensing has been utilized in applications such as fluid level sensing, determination of ion concentration, and for measuring the makeup of mixtures, such as oil and water. The conventional capacitive sensors are usually lacking in flexibility and difficult for total system integration.

From the above, it is seen that techniques for manufacturing improved MEMS devices is highly desirable.

BRIEF SUMMARY OF THE INVENTION

The present invention relates generally to micro fabrication techniques. More particularly, the invention provides a method and device for manufacturing a fluidic sensing device using a micromachining method and apparatus. Merely by way of example, the invention has been applied to the manufacture of a polymer based capacitive fluidic sensing device. But it would be recognized that the invention has a much broader range of applicability. For example, the invention can be applied to other applications.

In a specific embodiment, the invention provides a microfluidic device for capacitive pressure sensing. The device includes a fluid channel including an inlet at a first end and an outlet at a second end, a cavity region coupled to the fluid channel, and a polymer based membrane coupled between the fluid channel and the cavity region. Additionally, the device includes a first capacitor electrode coupled to the membrane, a second capacitor electrode coupled to the cavity region and physically separated from the first capacitor electrode by at least the cavity region, and an electrical power source coupled between the first capacitor electrode and the second capacitor electrode and causing an electric field at least within the cavity region. The polymer based membrane includes a polymer.

According to another embodiment of the present invention, a microfluidic device for capacitive fluidic sensing includes a fluid channel including an inlet at a first end and an outlet at a second end. The fluid channel is associated with a first polymer based layer and a second polymer based layer. Additionally, the device includes a first capacitor electrode coupled to the first polymer based layer. The second capacitor electrode is coupled to the second polymer based layer and physically separated from the first capacitor electrode by at least the fluid channel. Moreover, the device includes an electrical power source coupled between the first capacitor electrode and the second capacitor electrode and causing an electric field at least within the fluid channel. The first polymer based layer includes a first polymer, and the second polymer based layer includes a second polymer.

According to yet another embodiment of the present invention, a microfluidic device for capacitive fluidic sensing includes a fluid channel including an inlet at a first end and an outlet at a second end. The fluid channel is associated with a first polymer based layer and a second polymer based layer. Additionally, the device includes a first capacitor electrode coupled to the first polymer based layer, a second capacitor electrode coupled to the first polymer based layer and physically separated from the first capacitor electrode, and an electrical power source coupled between the first capacitor electrode and the second capacitor electrode and causing an electric field at least within the fluid channel. The first polymer based layer includes a first polymer, and the second polymer based layer includes a second polymer.

According to yet another embodiment of the present invention, a method for fabricating a capacitive fluidic sensing device includes providing a substrate, patterning a first electrode layer to form at least a first electrode overlying the substrate, and forming a first polymer based layer overlying the first electrode. Additionally, the method includes forming a first sacrificial layer overlying the first polymer based layer, forming a second polymer based layer overlying the first sacrificial layer, and patterning a second electrode layer to form at least a second electrode over the second polymer based layer. The second electrode is associated with the first electrode. Moreover, the method includes forming a third polymer based layer overlying the second electrode to sandwich the second electrode between the second polymer based layer and the third polymer based layer, forming a second sacrificial layer overlying the third polymer based layer, and forming a fourth polymer based layer overlying the second sacrificial layer. Also, the method includes releasing the first sacrificial layer between the first polymer based layer and the second polymer based layer, and releasing the second sacrificial layer between the second polymer based layer and the third polymer based layer.

According to yet another embodiment of the present invention, a method for fabricating a capacitive fluidic sensing device includes providing a substrate, patterning a first electrode layer to form at least a first electrode overlying the substrate, and forming a first polymer based layer overlying the first electrode. Additionally, the method includes forming a first sacrificial layer overlying the first polymer based layer, forming a second polymer based layer overlying the first sacrificial layer, and patterning a second electrode layer to form at least a second electrode over the second polymer based layer, the second electrode being associated with the first electrode. Moreover, the method includes forming a third polymer based layer overlying the second electrode to sandwich the second electrode between the second polymer based layer and the third polymer based layer and releasing the first sacrificial layer between the first polymer based layer and the second polymer based layer.

According to yet another embodiment of the present invention, a method for fabricating a capacitive fluidic sensing device includes providing a substrate, patterning a first electrode layer to form at least a first electrode and a second electrode overlying the substrate, the second electrode being associated with the first electrode, and forming a first polymer based layer overlying the first electrode and the second electrode. Additionally, the method includes forming a first sacrificial layer overlying the first polymer based layer, forming a second polymer based layer overlying the first sacrificial layer, and releasing the first sacrificial layer between the first polymer based layer and the second polymer based layer. The first electrode and the second electrode are two interlocking and physically separated electrodes.

Numerous benefits are achieved using the present invention over conventional techniques depending upon the embodiment. For example, some embodiments of the present invention provide a capacitive sensor with some or all advantages including versatility, flexibility, high sensitivity, small footprints, and easy integration. Certain embodiments of the present invention provide a capacitive sensor suitable for microfluidic applications based on high sensitivity and easy integration. The versatility of the Parylene/photoresist surface micromachining technology facilitates the integration of the sensor with other devices for the creation of an entire microfluidic systems. The sensor provides feedback for controlling the microfluidic system. Depending upon the embodiment, one or more of these benefits may be achieved. These and other benefits are provided throughout the present specification and more particularly below.

Various additional features and advantages of the present invention can be more fully appreciated with reference to the detailed description and accompanying drawings that follow.

BRIEF DESCRIPTION OF THE DRAWINGS

FIGS. 7(a) and 7(b) are simplified cross-sectional view diagrams illustrating a pressure sensor according to an embodiment of the present invention;

DETAILED DESCRIPTION OF THE INVENTION

Figure 1:
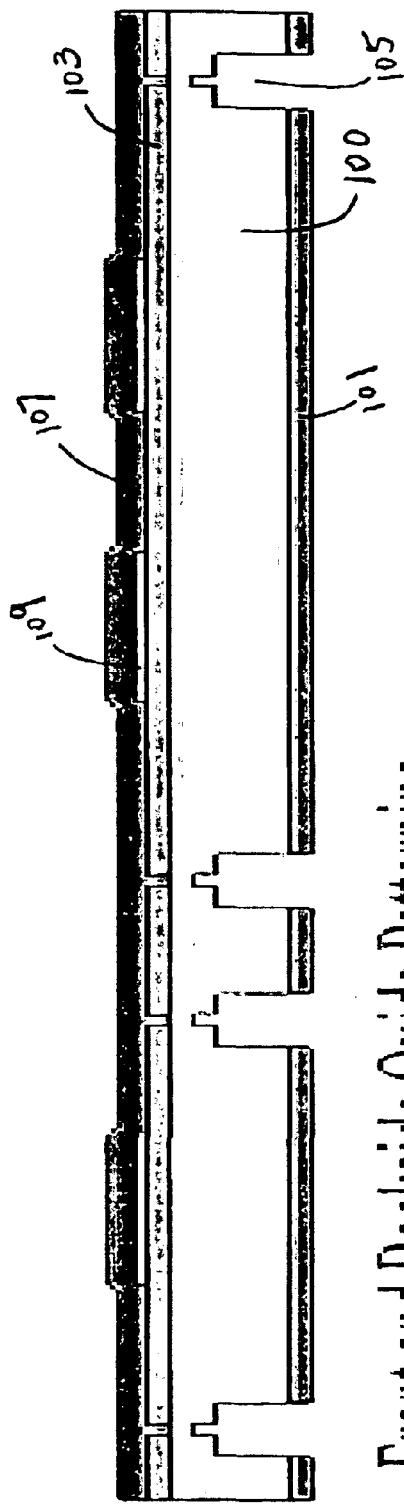
FIGS. 1–5 are simplified cross-sectional view diagrams illustrating a method for fabricating a capacitive sensing device according to an embodiment of the present invention.

The present invention relates generally to micro fabrication techniques. More particularly, the invention provides a method and device for manufacturing a fluidic sensing device using a micromachining method and apparatus. Merely by way of example, the invention has been applied to the manufacture of a polymer based capacitive fluidic sensing device. But it would be recognized that the invention has a much broader range of applicability. For example, the invention can be applied to other applications.

A method for fabricating a micro fluidic sensing device can be outlined as follows:

1. Provide a support substrate including backside and front side, e.g., silicon wafer;
2. Form an oxide layer (or other dielectric material layer or multi-layers) overlying the surfaces of the substrate;
3. Form a photolithographic pattern overlying the oxide layer;
4. Define openings in the oxide layer using the photolithographic pattern to pattern the backside of the substrate;
5. Deposit electrode layer overlying the front side of the substrate;
6. Pattern electrode layer to form a plurality of electrode structures;
7. Form first polymer based layer overlying the plurality of electrode structures;
8. Form silicon layer overlying the first polymer based layer;
9. Form first sacrificial layer overlying the patterned silicon layer;
10. Form second polymer based layer overlying the sacrificial layer;
11. Pattern second polymer based layer;
12. Form second electrode layer overlying the second polymer based layer;
13. Form third polymer based layer overlying the second electrode layer;
14. Form second sacrificial layer overlying the third polymer based layer;
15. Form fourth polymer based layer overlying the second sacrificial layer;
16. Open backside regions to the sacrificial layers;

17. Release sacrificial layers; and
18. Perform other steps, as desired.

The above sequence of processes provide a method of fabricating a capacitive sensor of polymer based material using micromachining techniques. As shown, the method uses a combination of front side patterning and backside patterning according to a specific embodiment. The method forms a sensing device that is composed of multiple polymer based materials. Preferably, the polymer based material is a Parylene material such as Parylene-C, but can be others. Additionally, certain processes may be combined, one or more processes may be added, and one or more processes may be removed, depending upon the embodiment. The sequence of the processes is changed in certain embodiments. Further details of the present method can be found throughout the present specification and more particularly below.

FIGS. 1–5 are simplified cross-sectional view diagrams illustrating a method for fabricating a capacitive sensing device according to an embodiment of the present invention. These diagrams are merely illustrations, which should not unduly limit the scope of the claims herein. One of ordinary skill in the art would recognize many variations, alternatives, and modifications.

As shown in FIG. 1, the method begins by providing a support substrate structure 100, e.g., silicon wafer, glass substrate, which has a surface and a thickness defined underlying the surface. The structure also includes oxide layers 101 and 103 overlying the surface of the substrate. The surface includes front side and backside. Although such oxide layer has been illustrated, such layer or layers may also include nitrides, a combination of oxide and nitride, and others, which serve as a hard mask to protect surfaces of the substrate 100. Preferably, the oxide layers 101 and 103 are formed using wet oxidation techniques such as steam oxidation and/or wet dipping, as well as others. Of course, one of ordinary skill in the art would recognize many variations, modifications, and alternatives.

The method forms a photolithographic pattern overlying the oxide layers 101 and 103. The pattern is often formed by coating the surface with a photosensitive material, which is exposed and then developed. Openings are formed in the photosensitive material. Such openings may correspond to trench regions or recessed regions to be formed in the substrate. Etching techniques are often used to form openings in the oxide layers 101 and 103 to expose substrate regions, which will be subjected to reactive ion etching processes or other directional etching processes. Preferably, deep reactive ion etching (DRIE), is used to form openings 105, as illustrated by FIG. 1, to define recessed regions or trenches, including sides and lower portions. The recessed regions extend toward the front surface of the substrate 100.

The method patterns an electrode layer 109 overlying the surface of the oxide layer 103. The electrode layer 109 is often a conductive material, such as a single layer or multiple layers. As merely an example, the conductive material can be Cr/Au material that is deposited. Other materials can also be used. The electrode layer 109 is often provided to a predetermined thickness. Preferably, the Cr/Au is deposited to a thickness of between about 100–3000 Å. The electrode layer 109 is patterned to form a plurality of electrode regions, which are separated from each other in preferred embodiments. The electrode layer has been or will be coupled to a voltage potential once the device has been completed.

The method forms a thickness of polymer based material 107 overlying the oxide layer 103, the patterned electrode layer 109, and the substrate 100. The polymer based material grows on the exposed surfaces of the substrate 100, the oxide layer 103, and the patterned electrode layer 109. Preferably, the polymer based material is Parylene, which is a commercial name for polymers that belong to a chemical family called poly-para-Xylylene. In the specific embodiment illustrated in FIG. 1, Parylene having a thickness of approximately 1 $\mu$m is formed. In another example, the thickness of the polymer based layer 107 ranges from 0.1 to 10 microns.

Parylene is often deposited using gaseous monomers. Such monomers are polymerized and deposited on the substrate, including the trench region, as a pinhole-free and stress-free solid film with selected physical, thermal, electrical, barrier, and biocompatible properties. As shown, Parylene is a conformal protective polymer coating material that conforms to surfaces of the substrate 100, the oxide layer 103, and the patterned electrode layer 109. Parylene exhibits dielectric strength, high surface and volume resistivities, and electrical properties that may be independent of temperature. It also provides a substantially conformal, pinhole-free coating that is corrosion resistance and provides dielectric protection. Before going to the next step, we shall briefly discuss deposition techniques of Parylene using a vacuum chemical vapor deposition process.

Parylene is often applied at a molecular level by a vacuum deposition process at ambient temperature or other temperatures. For example, the deposition process includes chemical vapor deposition at room temperature. The vacuum deposition process uses a vaporizer, a pyrolysis, and a deposition chamber. The deposition chamber is often coupled to cold trap, which is coupled to vacuum pump. The vacuum pump maintains vacuum in the chamber. Parylene can be applied at room temperature with certain vacuum deposition equipment that permits control of coating rate and thickness. The deposition process takes place at the molecular level as the chemical, in dimer form, is converted under vacuum and heat to dimeric gas, pyrolyzed to cleave the dimer, and deposited as a clear polymer film. Depending upon the embodiment, Parylene may come in one of a variety of forms such as Parylene C, Parylene N, and Parylene D, which correspond to three dimer variations. Each of the dimer variations could be suited to the requirements of a specific embodiment. Preferably, Parylene C is desirable. Further details of the deposition apparatus and characteristics of Parylene can be found at the website of ConformalCoating.com. Of course, there can also be other variations, modifications, and alternatives. Parylene can be patterned in oxygen plasma using photoresist or metal such as aluminum as mask.

Figure 2:
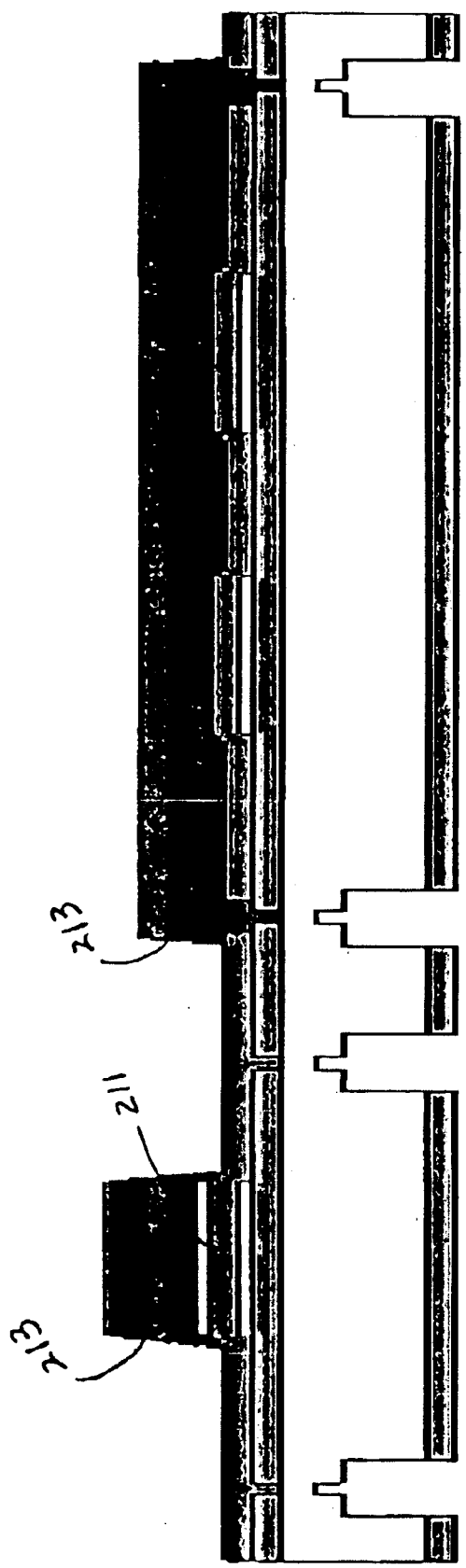

Referring now to FIG. 2, the method includes forming a silicon layer 211. The silicon layer can be formed using chemical vapor deposition or other techniques. Preferably, the silicon layer is provided at low temperature. In the specific embodiment shown in FIG. 2, a silicon layer having a thickness of approximately 3000 Å is formed by physical vapor deposition (sputtering). The silicon layer is patterned to remain over a certain portion of the polymer based material overlying a certain electrode.

Next, the method form a sacrificial layer 213 overlying the silicon layer 211, the polymer based material 107, the oxide layer 103, and the substrate 100. The sacrificial layer 213 is preferably any material that can be easily removed at a later process. Preferably, the sacrificial layer is a polymer based material that can dissolve. Such material can be photoresist or other like material. In the specific embodiment shown in FIG. 2, a photoresist layer having a thickness of about 4 µm is patterned. In another example, the thickness of the sacrificial layer 213 ranges from 0.1 to 100 microns. The sacrificial layer 213 can be formed at a temperature less than 120° C. or at other temperature.

Figure 3:
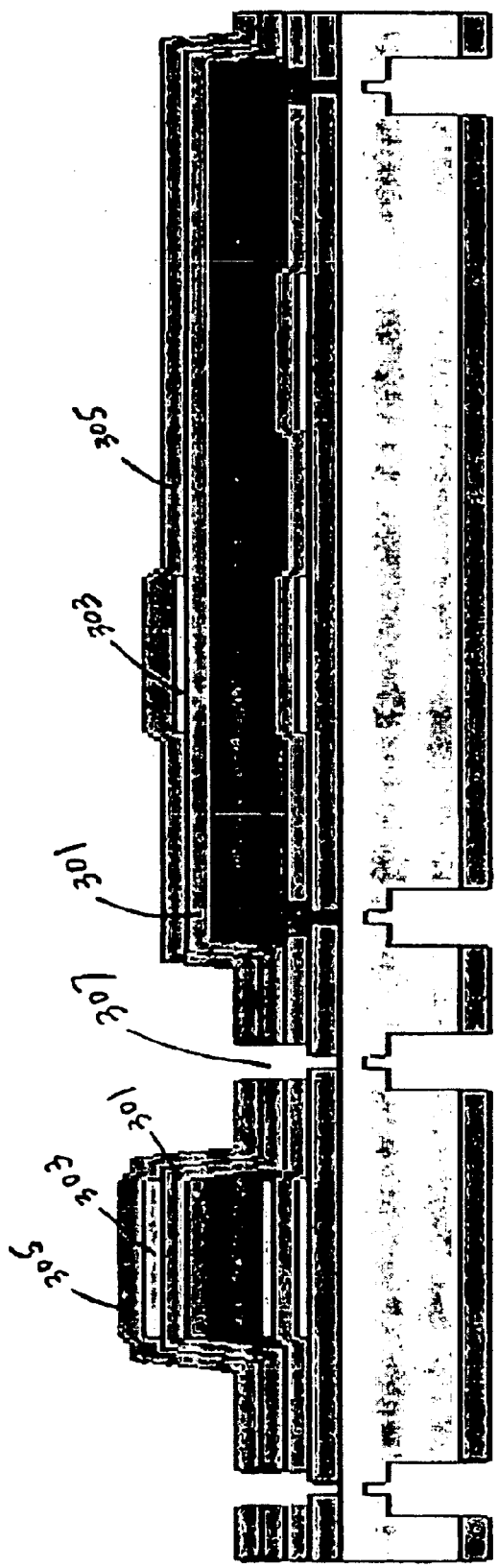

Turning now to FIG. 3, the method forms a sandwiched structure that includes a second electrode element. The sandwiched structure includes a first polymer based material 301, overlying electrode material 303, and an overlying polymer based material 305. Preferably, the polymer based material is Parylene, and materials 301 and 305 are deposited in the manner described above.

As shown in FIG. 3, the electrode material 303 is sandwiched between the polymer based materials 301 and 305. In the specific embodiment shown in FIG. 3, the patterned second electrodes 303 comprising Cr/Au are sandwiched between Parylene layers 301 and 305. For example, the Parylene layers 301 and 305 each have a thicknesses of about 1 µm, and the patterned second electrodes 303 each have a thickness ranging from 100 Å to 1500 Å. In another example, the thickness of the polymer based layer 301 ranges from 0.1 to 10 microns. In yet another example, the thickness of the polymer based layer 305 ranges from 0.1 to 10 microns.

Openings 307 are formed overlying the substrate 100 within the polymer based materials. The opening will be used to release an overlying sacrificial layer, which will be applied for the fluidic chamber.

Figure 4:
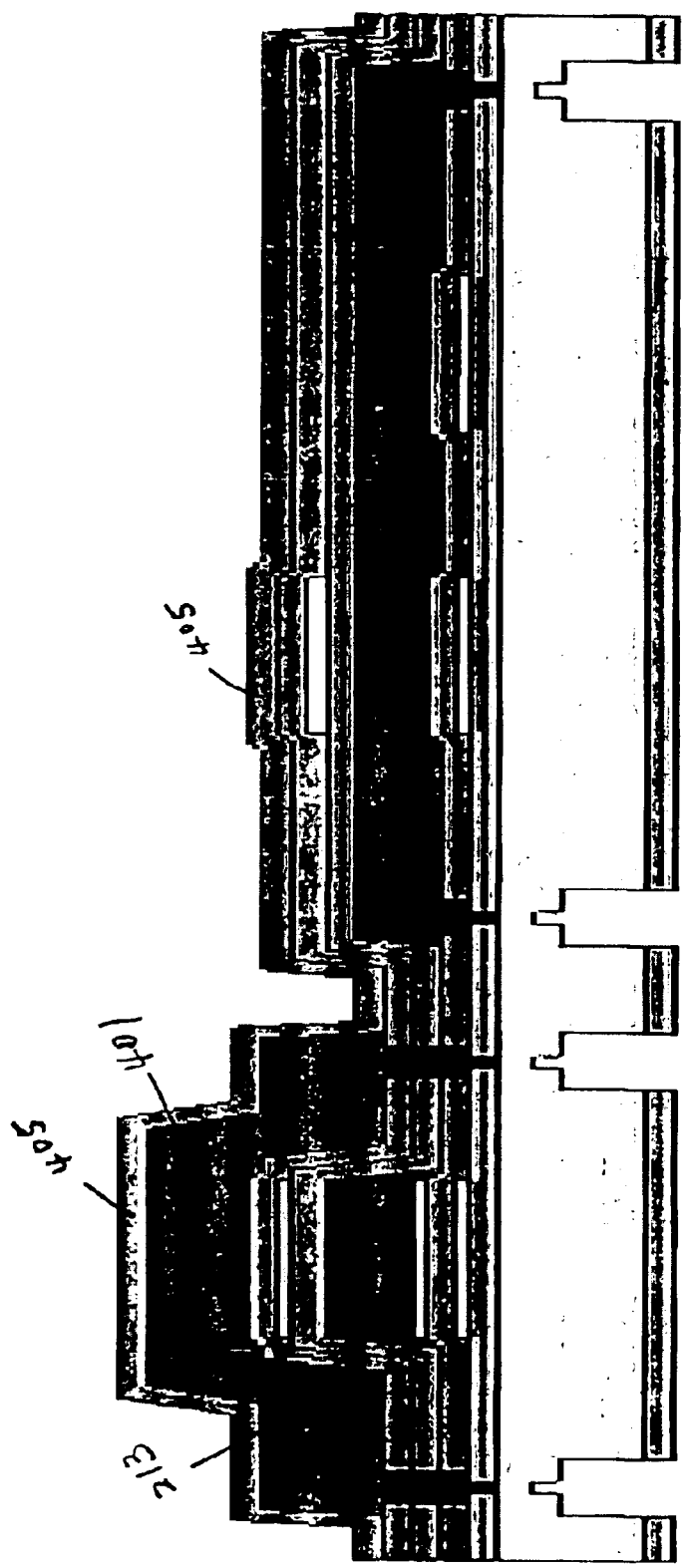

Referring now to FIG. 4, the method includes forming a sacrificial layer 401 overlying the sandwiched structure. The sacrificial layer is preferably any material that can be easily removed at a later process. Preferably, the sacrificial layer is a polymer based material that can dissolve. Such material can be photoresist or other like material. The sacrificial layer 401 can be formed at a temperature less than 120° C. or at other temperature.

The sacrificial layer will occupy a region corresponding to a fluid chamber for the present device. As shown, the sacrificial layer 401 extends to opening 307, which will be used to introduce solvent to release the sacrificial layer. In the specific embodiment shown in FIG. 4, a photoresist layer having a thickness of about 5 µm is formed. In another example, the thickness of the sacrificial layer 401 ranges from 1 to 10 microns.

Overlying the sacrificial layer 401 is a polymer based material 405. Preferably, the polymer based material 405 is Parylene. In the specific embodiment shown in FIG. 4, a Parylene layer having a thickness of about 1 µm is formed. In another example, the thickness of the polymer-based layer 405 ranges from 0.1 to 10 microns. Parylene can be patterned in oxygen plasma using photoresist or metal such as aluminum as mask.

Figure 5:
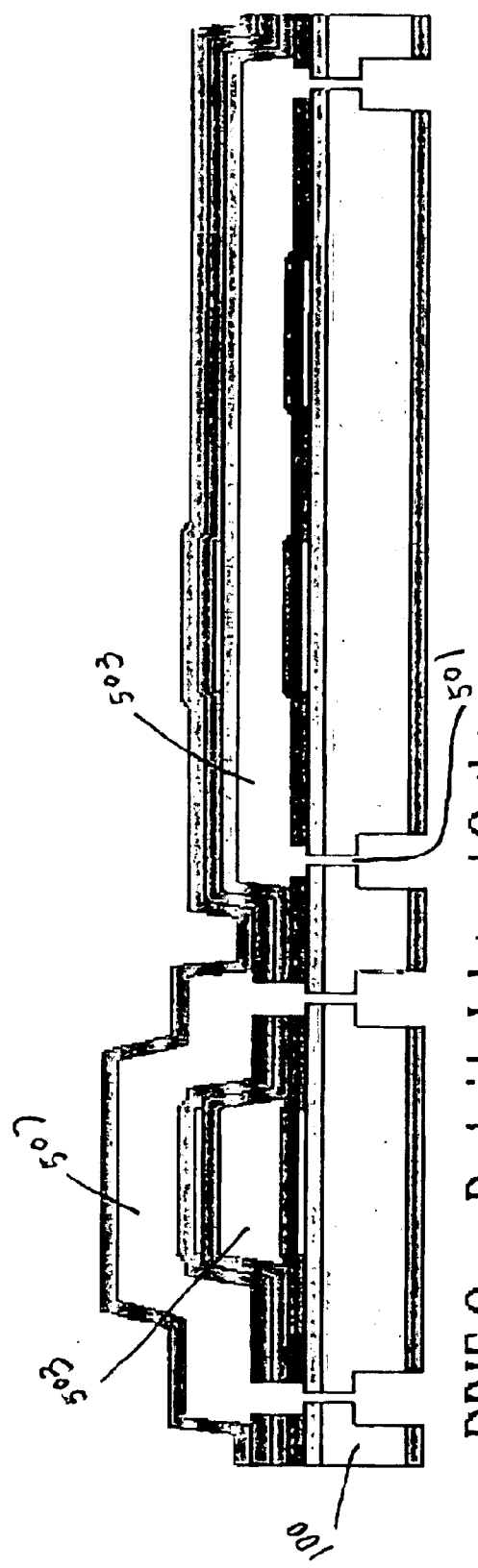

The method then releases the sacrificial layers 213 and 401, as illustrated by FIG. 5. First, an etching process removes material from the backside of the substrate 100 to form openings 501, which extend through the substrate 100 and exposes the sacrificial material. Once the sacrificial material has been exposed, solvents and/or etchants are used to dissolve the sacrificial layers and remove them from chamber regions 503 and 507. For example, the chamber region 503 has a diameter ranging from 10 to 1000 microns. In another example, the chamber region 503 has a diameter equal to 100 microns. In yet another example, the chamber region 503 has a height ranging from 0.1 to 100 microns. In yet another example, the chamber region 503 has a height ranging from 1 to 10 microns. In yet another example, the chamber region 503 has a height equal to 4 microns. In yet another example, the chamber region 503 has a width ranging from 1 to 1000 microns.

In accordance with one specific embodiment wherein the sacrificial material comprises photoresist, this material is removed by exposure to acetone. Prolonged acetone soaking, however, may result in delamination between Parylene layers. So as soon as most of photoresist is dissolved, the chips were transferred to Isopropyl Alcohol (IPA) for further cleaning.

Once the photoresist sacrificial layers 213 and 401 have been removed by exposure to liquid acetone and IPA, the silicon sacrificial material 211 is removed by exposure to a gaseous etchant such as $BrF_3$. In this embodiment, the role of the silicon sacrificial layer 211 is to provide the final release of the membrane in a gaseous environment, without resulting stiction produced by release in a liquid environment.

Figure 6:
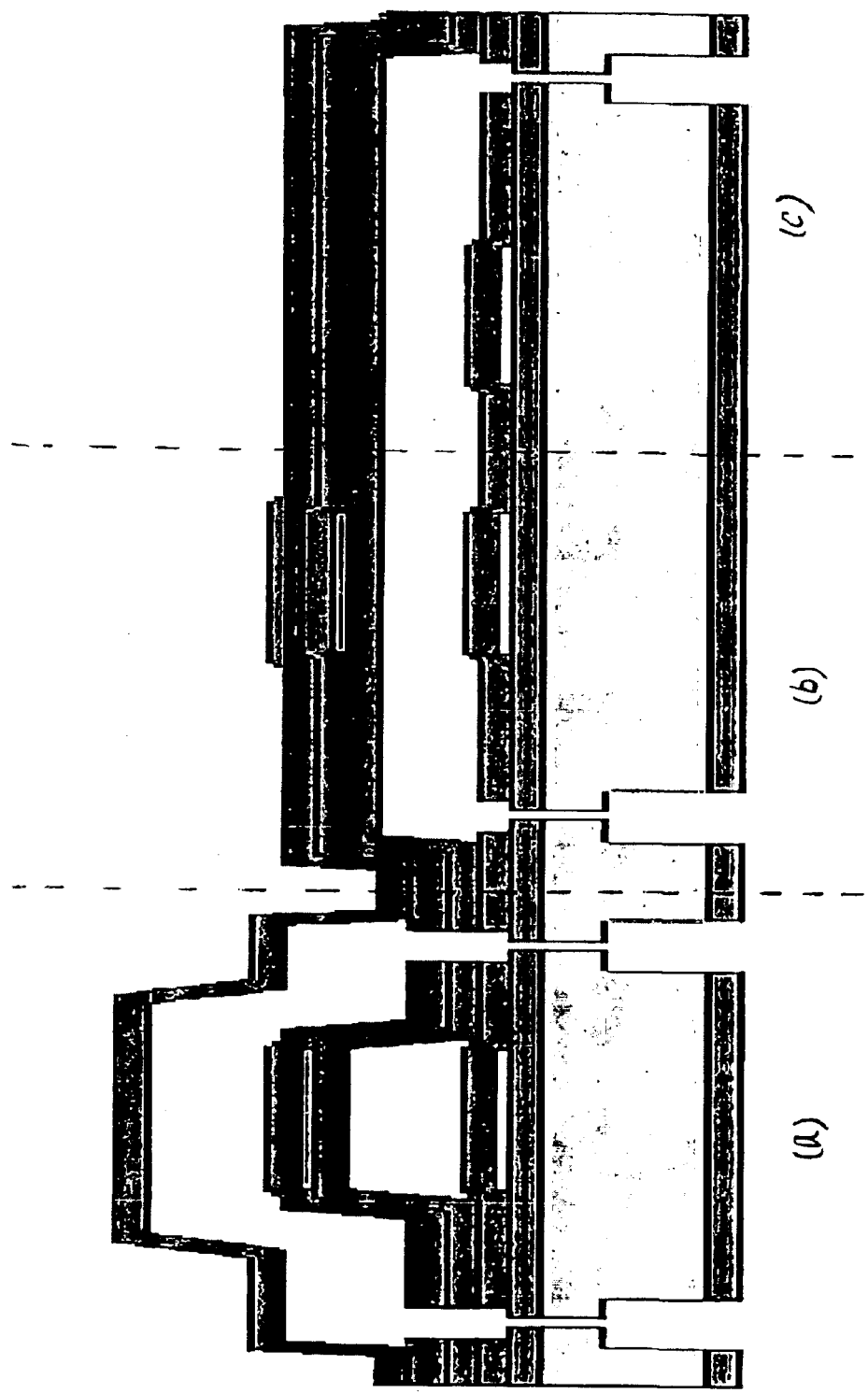
FIGS. 6(a), 6(b), and 6(c) are simplified capacitive sensors according to an embodiment of the present invention.

FIGS. 6(*a*), 6(*b*), and 6(*c*) are simplified capacitive sensors according to an embodiment of the present invention. These diagrams are merely illustrations, which should not unduly limit the scope of the claims herein. One of ordinary skill in the art would recognize many variations, alternatives, and modifications. For example, each of the polymer based layers 107, 301, 305 and 405 include a material selected from the group consisting of Parylene, polyimide, and silicone. In another example, each of the electrode layers 109 and 303 includes a material selected from the group consisting of gold, aluminum, platinum, chrome, titanium, and doped polysilicon. Additionally, the electrode layers 109 and 303 are usually each coupled to the same electrical power source, which causes an electric field in the chamber 503.

The capacitive sensors in FIGS. 6(*a*), 6(*b*) and 6(*c*) are a pressure sensor, a parallel plate sensor, and an interdigitated sensor respectively. These sensors may be made by the method as shown in FIGS. 1–5. The processes in FIGS. 1–5 are provided for all three types of sensors, but some processes may be skipped for certain types of sensors. Also, some processes may serve different purposes for various types of sensors. For example, depositing and patterning the electrode layer 109 defines the bottom electrodes of the pressure sensor and the parallel plate sensor in FIGS. 6(*a*) and 6(*b*). This process defines both electrodes for the interdigitated sensor in FIG. 6(*c*). In another example, forming the sacrificial layer 213 defines the capacitive air gap for the pressure sensor in FIG. 6(*a*) and defines the microchannel in which the parallel sensor and the interdigitated sensor in FIGS. 6(*b*) and 6(*c*) are integrated. In yet another example, forming and patterning the electrode layer 303 produces the top electrodes of the pressure sensor and the parallel plate sensor in FIGS. 6(*a*) and 6(*b*), but this process can be skipped for the interdigitated sensor in FIG. 6(*c*). In yet another example, forming and patterning the sacrificial layer 401 defines the channel above the pressure sensor in FIG. 6(*a*), but this process may be skipped for the parallel plate sensor and the interdigitated sensor in FIGS. 6(*b*) and 6(*c*). In yet another example, the processes of forming and releasing the silicon layer 211 can produce a freestanding membrane for the pressure sensor in FIG. 6(*a*), but these processes may be skipped for the parallel plate sensor and the interdigitated sensor in FIGS. 6(*b*) and 6(*c*). In yet another example, forming the polymer based layer 405 may be skipped for the parallel plate sensor and the interdigitated sensor in FIGS. 6(*b*) and 6(*c*). In yet another example, forming the polymer based layer 305 may be skipped for the interdigitated sensor in FIG. 6(*c*).

Further details of the present device including additional fabrication techniques can be found throughout the present specification and more particularly below.

FIGS. 7(a) and 7(b) are simplified cross-sectional view diagrams illustrating a pressure sensor according to an embodiment of the present invention. These diagrams are merely illustrations, which should not unduly limit the scope of the claims herein. One of ordinary skill in the art would recognize many variations, alternatives, and modifications. The pressure sensor 700 includes the oxide layer 101, the substrate 100, the oxide layer 103, the electrode 109, the polymer based layer 107, the polymer based layer 301, the electrode 303, the polymer based layer 305, the polymer based layer 405, the cavity 503, and the channel 507. Although the above has been shown using components 101, 100, 103, 109, 107, 301, 303, 305, 405, 503 and 507, there can be many alternatives, modifications, and variations. Some of the components may be combined. Other components may be added to the pressure sensor 700. Depending upon the embodiment, one or more of the components may be replaced or removed. For example, the oxide layer 101 and/or the substrate 100 is removed. Further details of these components are found throughout the present specification including FIGS. 1–5 and 6(a) and more particularly below.

The pressure sensor 700 is realized by creating a cavity 503 beneath the channel 507. For example, the cavity has a height ranging from 0.1 to 10 microns. In another example, the cavity has a height equal to 5 microns. The upper electrode 303 is sandwiched between the floor 305 of the channel 507 and another polymer based layer 301. The upper electrode 303, the floor 305 and the polymer based layer 301 form a composite membrane. For example, the composite membrane has a 200-μm diameter in the top view as shown in FIG. 7(b). The bottom electrode 109 is fixed on the oxide layer 103 and the substrate 100. In another example, the composite membrane has a diameter ranging from 10 to 1000 microns. In yet another example, the composite membrane has a thickness ranging from 0.1 to 10 microns. In yet another example, the composite membrane has a thickness ranging from 1 to 5 microns. In yet another example, the composite membrane has a thickness equal to 2 microns.

According to another embodiment of the present invention, the device 700 for capacitive sensing includes a fluid channel including an inlet at a first end and an outlet at a second end, a cavity region coupled to the fluid channel, and a polymer based membrane coupled between the fluid channel and the cavity region. Additionally, the device includes a first capacitor electrode coupled to the membrane, a second capacitor electrode coupled to the cavity region and physically separated from the first capacitor electrode by at least the cavity region, and an electrical power source coupled between the first capacitor electrode and the second capacitor electrode and causing an electric field at least within the cavity region. The polymer based membrane includes a polymer.

Figure 8:
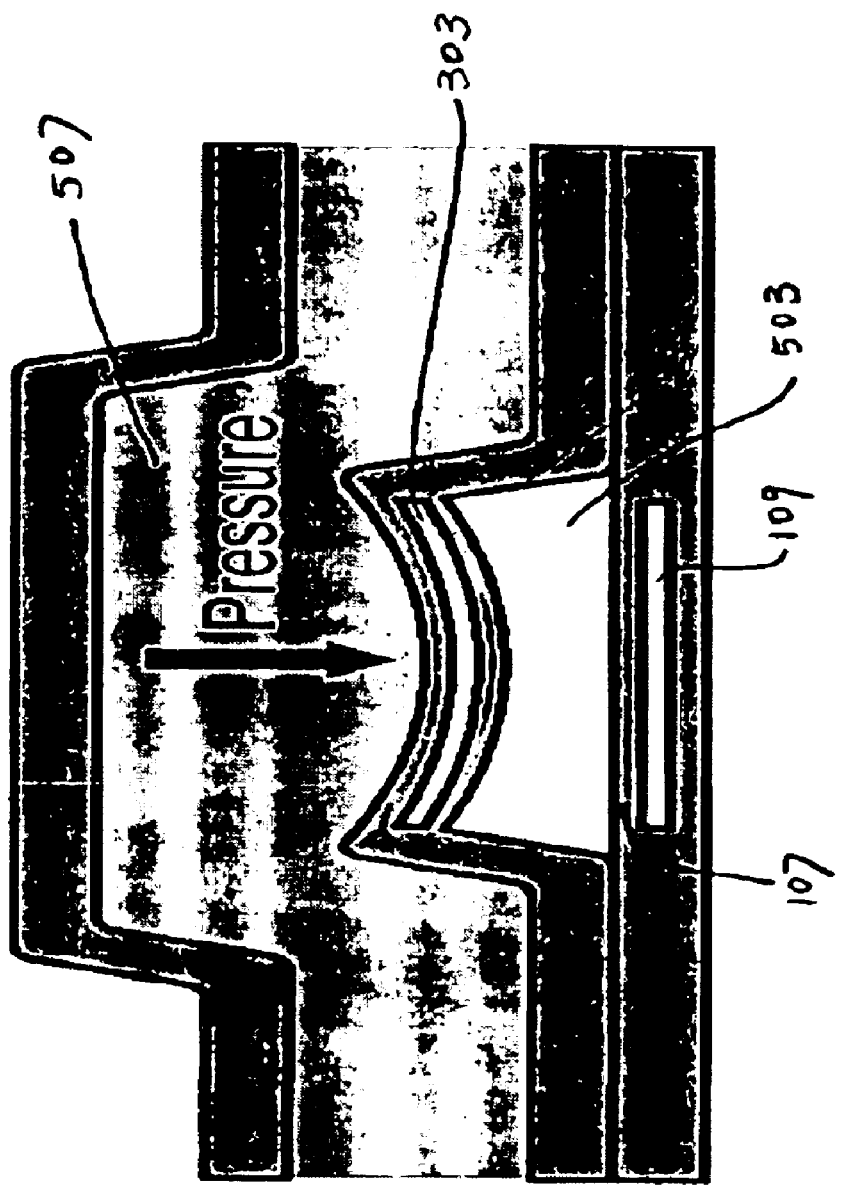
FIG. 8 shows the operation principle of a pressure sensor according to an embodiment of the present invention.

FIG. 8 shows the operation principle of the pressure sensor 700 according to an embodiment of the present invention. The diagram is merely an illustration, which should not unduly limit the scope of the claims herein. One of ordinary skill in the art would recognize many variations, alternatives, and modifications. Changes in the local channel pressure causes a deflection of the composite membrane including the electrode 303. The capacitance related to the cavity 503 and the electrodes 303 and 109 varies as a function of the local pressure in the channel 507. For example, the cavity contains air and is not sealed, making the sensor 700 a differential pressure sensor. The capacitive element is completely underneath the channel 507, the pressure reading is independent of the fluid being carried in the channel 507. For example, the pressure sensor 700 can measure a pressure ranging from 0 to 35 kPa with a resolution of 0.03 kPa. Additionally, the pressure sensor can function as a flow sensor based on a differential-pressure principle. In another example, the cavity contains a liquid.

Figure 9:
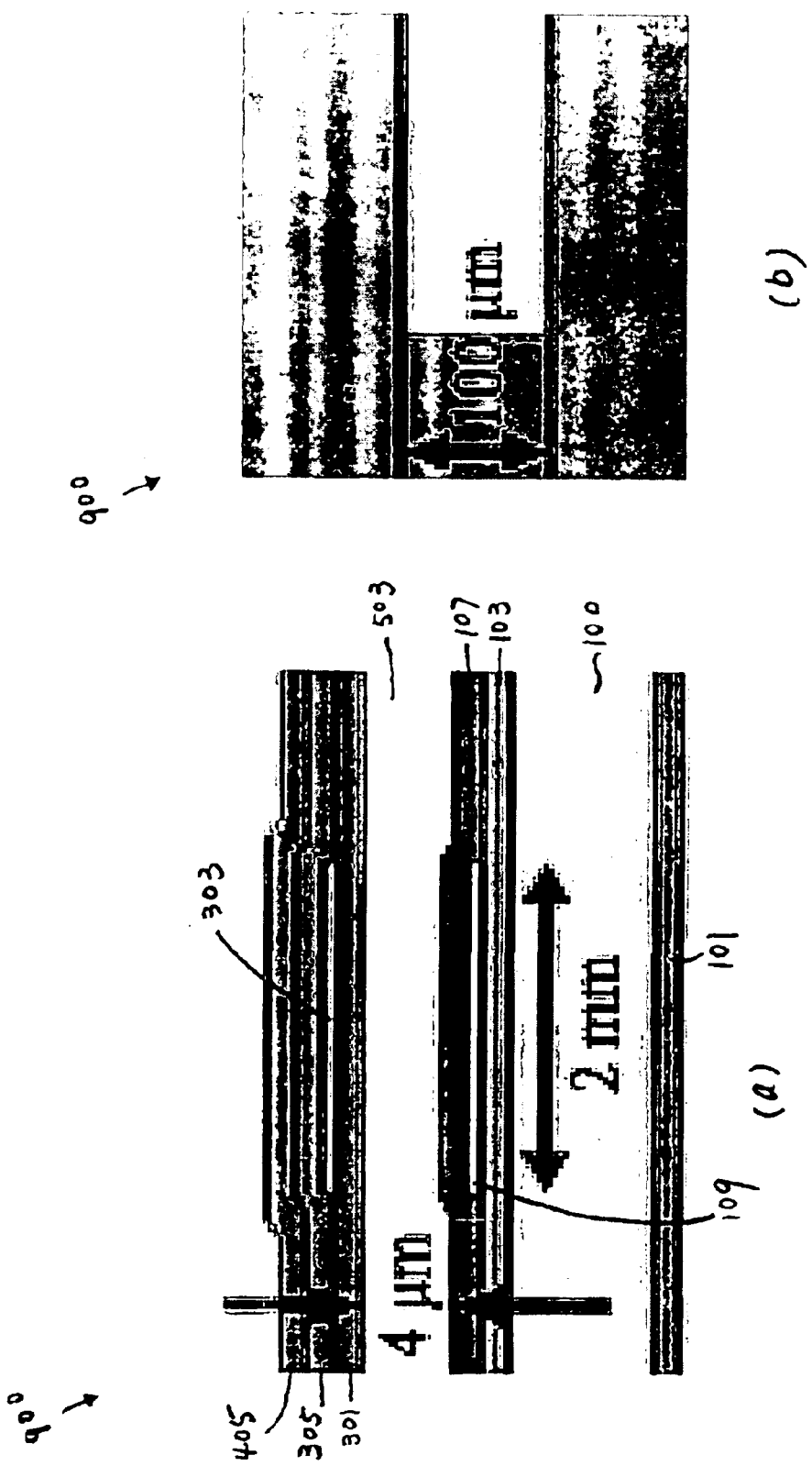
FIGS. 9(a) and 9(b) are simplified cross-sectional view diagrams illustrating a parallel plate sensor according to an embodiment of the present invention.

FIGS. 9(a) and 9(b) are simplified cross-sectional view diagrams illustrating a parallel plate sensor according to an embodiment of the present invention. These diagrams are merely illustrations, which should not unduly limit the scope of the claims herein. One of ordinary skill in the art would recognize many variations, alternatives, and modifications. The parallel plate sensor 900 includes the oxide layer 101, the substrate 100, the oxide layer 103, the electrode 109, the polymer based layer 107, the polymer based layer 301, the electrode 303, the polymer based layer 305, the polymer based layer 405, and the channel 503. Although the above has been shown using components 101, 100, 103, 109, 107, 301, 303, 305, 405 and 503, there can be many alternatives, modifications, and variations. Some of the components may be combined. Other components may be added to the pressure sensor 900. Depending upon the embodiment, one or more of the components may be replaced or removed. For example, the oxide layer 101 and/or the substrate 100 is removed. Further details of these components are found throughout the present specification including FIGS. 1–5 and 6(b) and more particularly below.

The parallel plate sensor 900 includes two electrodes 109 and 303, one placed in the roof of the channel 503 and the other placed in the floor of the channel 503. For example, the channel 503 has a height equal to 4 μm. The channel 503 and the electrodes 109 and 303 each have a width equal to 100 μm as shown in the top view in FIG. 9(b). The electrodes 109 and 303 each are 2 mm long. The electrodes 109 and 303 are electrically isolated from the fluid in the channel 503 with polymer based layers 107 and 301 respectively. For example, each of the polymer based layers 107 and 301 is a 1-μm Parylene layer. In another example, the electrodes 109 and 303 each have a length ranging from 10 microns to 10 mm.

A change in the dielectric constant of the channel fluid usually causes a capacitance change. Properties such as the mixing ratio of two pure liquids can be determined through appropriate calibration based on the effective dielectric constant as a function of the mixing ratio. Also, pure liquids can be identified provided they have different dielectric constants. Additionally, the parallel plate sensor 900 can function as a flow sensor based on a differential-pressure principle. Moreover, the parallel plate sensor 900 can be used to easily determine whether a particular channel is filled.

According to another embodiment of the present invention, the device 900 for capacitive sensing includes a fluid channel including an inlet at a first end and an outlet at a second end. The fluid channel is associated with a first polymer based layer and a second polymer based layer. Additionally, the device includes a first capacitor electrode coupled to the first polymer based layer. The second capacitor electrode is physically separated from the first capacitor electrode by at least the fluid channel. Moreover, the device includes an electrical power source coupled between the first capacitor electrode and the second capacitor electrode and causing an electric field at least within the fluid channel. The first polymer based layer includes a first polymer, and the second polymer based layer includes a second polymer.

According to an embodiment of the present invention, the fluid channel 503 of the device 900 is associated with a fluid volume. The fluid volume is associated with a capacitance of a capacitor including the first capacitor electrode, the second capacitor and the fluid channel. According to another embodiment of the present invention, the fluid channel 503 is associated with a fluid. The fluid is associated with a capacitance of a capacitor including the first capacitor electrode, the second capacitor and the fluid channel. The capacitance is associated with at least a characteristic of the fluid. The characteristic of the fluid is a dielectric constant, a conductivity, or a composition of the fluid. The fluid comprises a mixture of a plurality of solvents. For example, the mixture comprises at least one solvent selected from a group consisting of water, IPA, acetonitrile, acetone, methanol, and ethanol.

Figure 10:
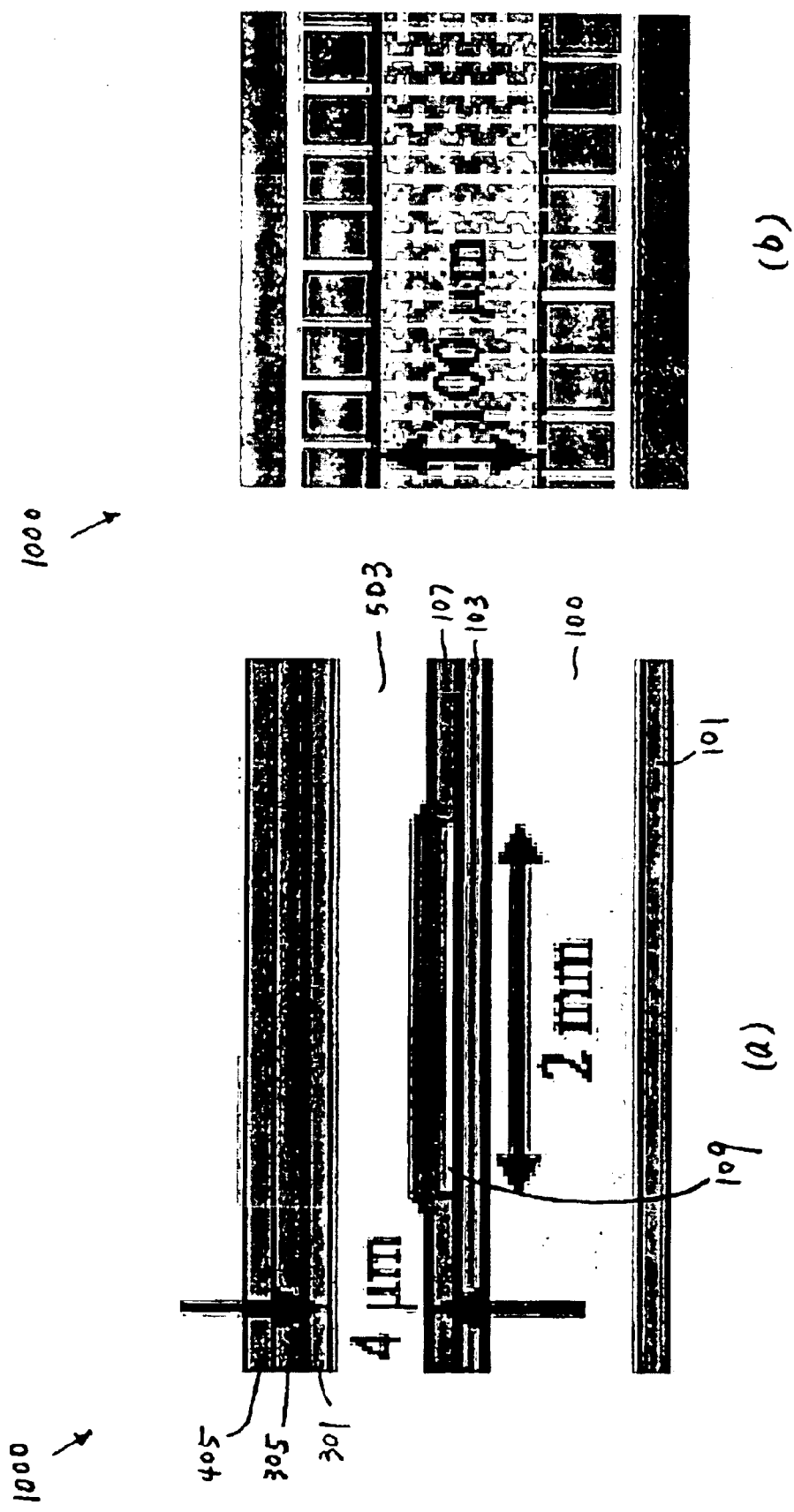
FIGS. 10(a) and 10(b) are simplified cross-sectional view diagrams illustrating an interdigitated sensor according to an embodiment of the present invention.

FIGS. 10(a) and 10(b) are simplified cross-sectional view diagrams illustrating an interdigitated sensor according to an embodiment of the present invention. These diagrams are merely illustrations, which should not unduly limit the scope of the claims herein. One of ordinary skill in the art would recognize many variations, alternatives, and modifications. The interdigitated sensor 1000 includes the oxide layer 101, the substrate 100, the oxide layer 103, the electrode 109, the polymer based layer 107, the polymer based layer 301, the polymer based layer 305, the polymer based layer 405, and the channel 503. Although the above has been shown using components 101, 100, 103, 109, 107, 301, 305, 405 and 503, there can be many alternatives, modifications, and variations. Some of the components may be combined. Other components may be added to the interdigitated sensor 1000. Depending upon the embodiment, one or more of the components may be replaced or removed. For example, the oxide layer 101 and/or the substrate 100 is removed. Further details of these components are found throughout the present specification including FIGS. 1–5 and 6(c) and more particularly below.

The interdigitated sensor 1000 includes the electrode 109 which comprises two interlocking comb-shaped electrodes as shown in the top view in FIG. 10(b). Both electrodes are placed directly beneath the floor of the channel 503. For example, the spacing between adjacent fingers is 15 $\mu$m and the electrodes overlap by 100 $\mu$m, also the width of the channel 503. The channel height is 4 $\mu$m and the total sensor length is 2 mm. The electrodes are insulated from the channel 503 with the polymer based layer 107. For example, the polymer based layer 107 is a 1-$\mu$m Parylene layer. The fringing electric field reaches into the channel 503, and a change in the dielectric constant of the channel fluid causes a capacitance change. In another example, the total sensor length ranges from 10 microns to 10 mm. In yet another example, the width of each finger ranges from 1 to 100 microns. In yet another example, the spacing between adjacent fingers ranges from 1 to 100 microns. In yet another example, the electrodes overlap by a distance ranging from 1 to 100 microns.

Properties such as the mixing ratio of two pure liquids can be determined through appropriate calibration based on the effective dielectric constant as a function of the mixing ratio. Also, pure liquids can be identified provided they have different dielectric constants. Additionally, the interdigitated sensor 1000 can be used to easily determine whether a particular channel is filled. Moreover, the interdigitated sensor 1000 can be used to monitor fluid front position. As a column of liquid flows into an empty channel, a predictable increase in capacitance may be observed. This capacitance is a function of the fluid front position, which gives a direct measurement of volume. For example, the interdigitated sensor 1000 can measure a volume ranging from 0 to 800 pL with a resolution no larger than 5 pL.

According to another embodiment of the present invention, the device 1000 for capacitive sensing includes a fluid channel including an inlet at a first end and an outlet at a second end. The fluid channel is associated with a first polymer based layer and a second polymer based layer. Additionally, the device includes a first capacitor electrode coupled to the second polymer based layer, a second capacitor electrode coupled to the second polymer based layer and physically separated from the first capacitor electrode, and an electrical power source coupled between the first capacitor electrode and the second capacitor electrode and causing an electric field at least within the fluid channel. The first polymer based layer includes a first polymer, and the second polymer based layer includes a second polymer.

According to an embodiment of the present invention, the fluid channel 503 of the device 1000 is associated with a fluid volume. The fluid volume is associated with a capacitance of a capacitor including the first capacitor electrode, the second capacitor and the fluid channel. According to another embodiment of the present invention, the fluid channel 503 is associated with a fluid. The fluid is associated with a capacitance of a capacitor including the first capacitor electrode, the second capacitor and the fluid channel. The capacitance is associated with at least a characteristic of the fluid. The characteristic of the fluid is a dielectric constant, a conductivity, or a composition of the fluid. The fluid comprises a mixture of a plurality of solvents. For example, the mixture comprises at least one solvent selected from a group consisting of water, IPA, acetonitrile, acetone, methanol, and ethanol.

Various experiments have been performed on the pressure sensor 700, the parallel plate sensor 900, and the interdigitated sensor 1000. According to one embodiment of the present invention, the pressure sensor 700 is calibrated using a regulated pressure source. A pressure is applied to both ends of the channel 507 simultaneously. For example, the application of pressure uses a custom-built Plexiglas jig. The pressure level is varied and the changing capacitance is measured. For example, capacitances are measured using a commercially available integrated circuit, such as Microsensors UCR MS3110.

Figure 11:
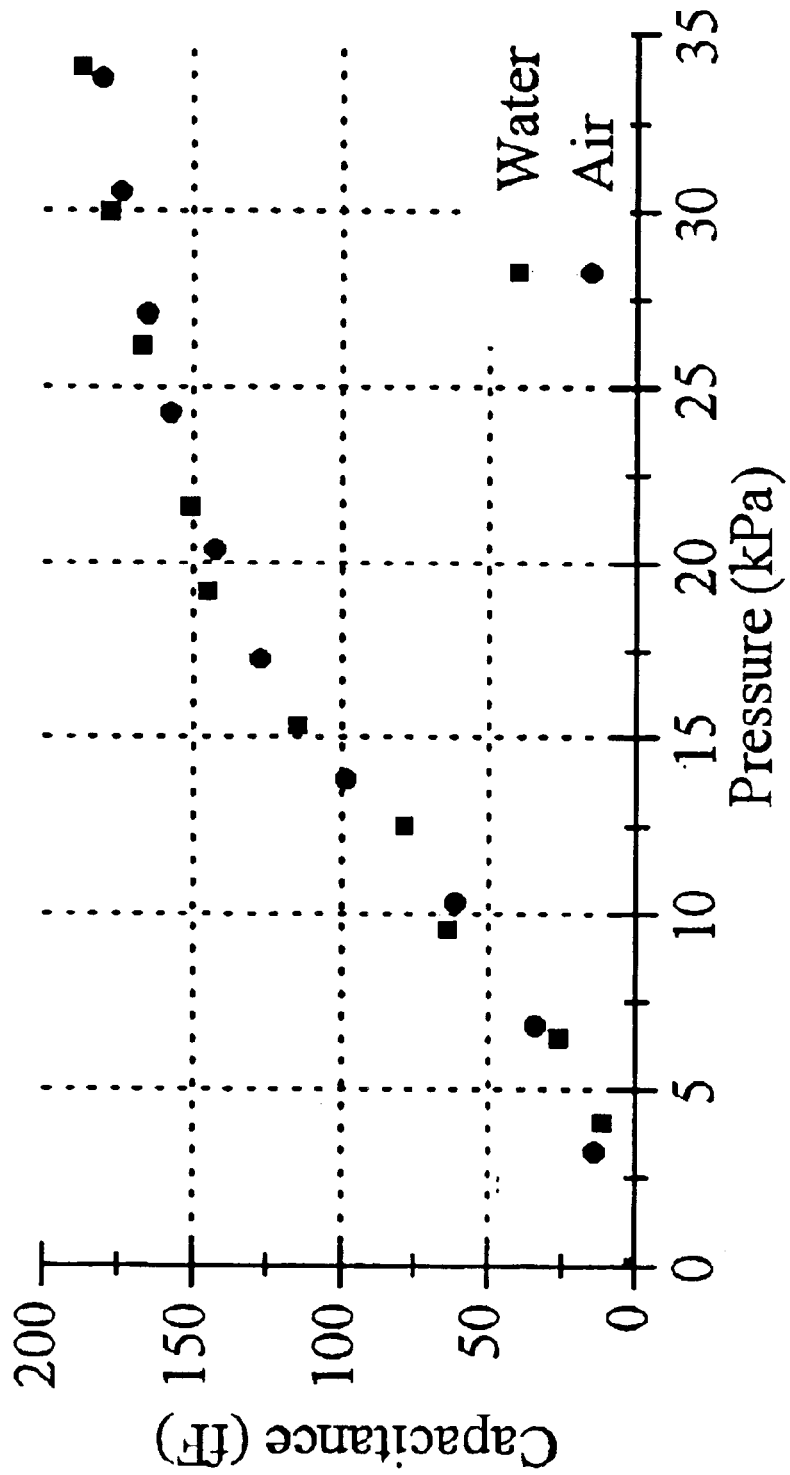
FIG. 11 is a simplified diagram showing capacitance as a function of pressure for a pressure sensor according to an embodiment of the present invention.

FIG. 11 is a simplified diagram showing capacitance as a function of pressure for the pressure sensor 700 according to an embodiment of the present invention. This diagram is merely an illustration, which should not unduly limit the scope of the claims herein. One of ordinary skill in the art would recognize many variations, alternatives, and modifications. The calibrations of the pressure sensor 700 is performed using either water or air as the channel fluid. As shown in FIG. 11, the pressure sensor 700 has a resolution equal to about 0.03 kPa and an accuracy equal to about 1.0 kPa.

Also shown in FIG. 11, the response of the pressure sensor 700 exhibits a roughly linear increase in capacitance at pressures below 20 kPa. At higher pressures, the sensitivity decreases and the capacitance begins to plateau. This is likely caused by the membrane bottoming out. To investigate the pressure sensor behavior more thoroughly, the deflection of the top electrode is measured at various applied pressures. For example, the measurement is performed with a WYKO NT2000 Optical Profiler.

Figure 12:
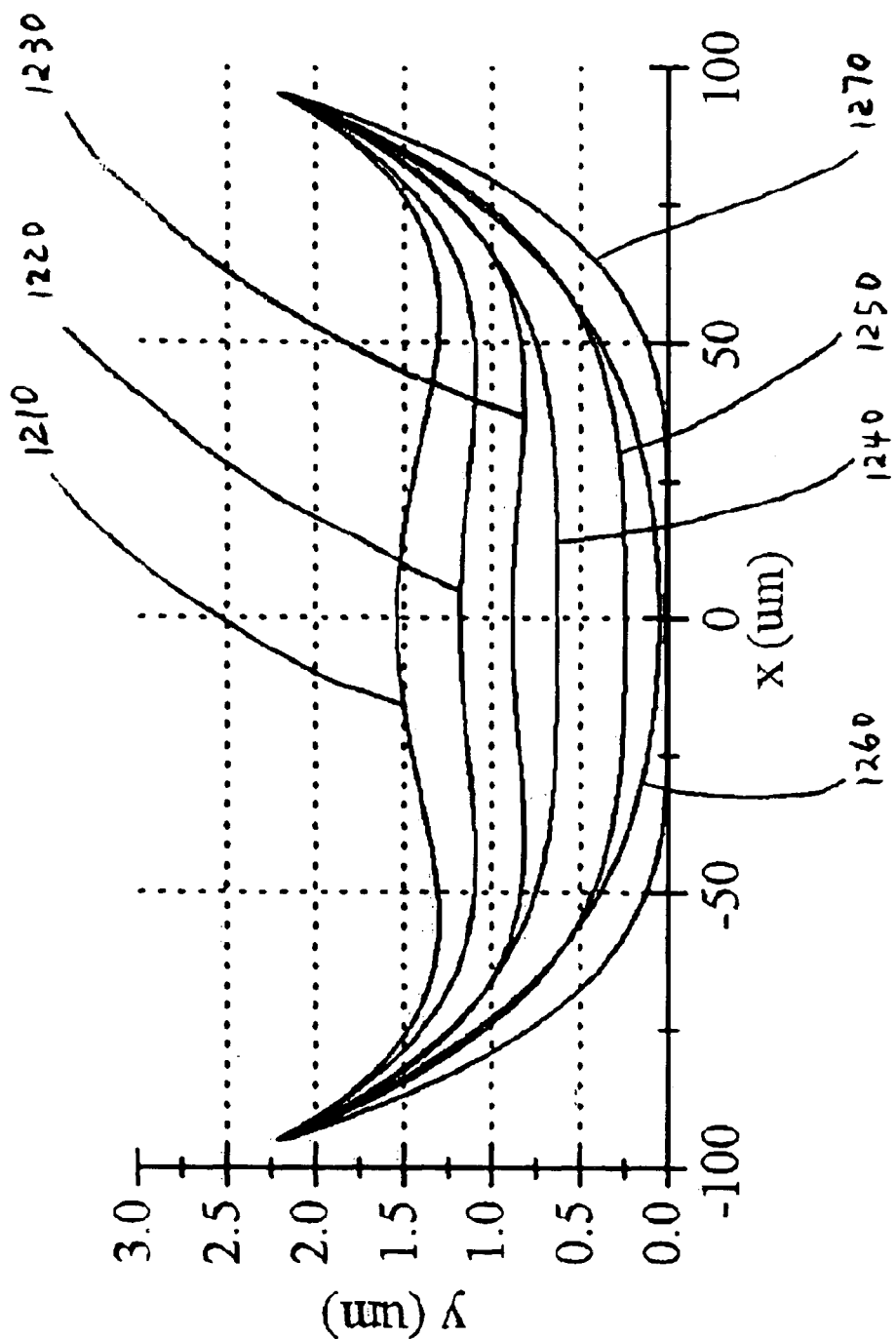
FIG. 12 is a simplified membrane profile for a pressure sensor at different pressures according ton an embodiment of the present invention.

FIG. 12 is a simplified membrane profile for the pressure sensor 900 at different pressures according ton an embodiment of the present invention. This diagram is merely an illustration, which should not unduly limit the scope of the claims herein. One of ordinary skill in the art would recognize many variations, alternatives, and modifications. The membrane profile includes curves 1210, 1220, 1230, 1240, 1250, 1260 and 1270 corresponding to pressures equal to 0.00, 3.45, 7.03, 10.62, 13.65, 17.23, 24.26 kPa respectively. As shown in FIG. 12, the initial membrane at 0.00 kPa is not flat, but instead the membrane exhibits a large downward deflection with the center of the membrane slightly bowed upward. This may signal certain distortion of the membrane caused by the fabrication process. For example, the distortion may occur during the drying process. After releasing the sacrificial layers, stiction may occur betweens the floor 107 of the cavity 503 and the composite membrane. The composite membrane includes the upper electrode 303, the floor 305 and the polymer based layer 301. The forces exerted on the composite membrane during drying may have been high enough to permanently deform the membrane.

According to one embodiment of the present invention, the fabrication of the pressure sensor 700 uses a 4-$\mu$m photoresist layer to define the cavity 503. The measurements as shown in FIG. 12 indicate a total deflection of only 1.5 $\mu$m. The discrepancy between 4 $\mu$m and 1.5 $\mu$m may be caused by the distortion of the composite membrane. This distortion decreases the pressure range of the sensor 700. Also, the measurements in FIG. 12 indicate that the composite membrane bottoms out at approximately 20 kPa. This coincides precisely with the measured sensor response as shown in FIG. 11.

A test of the pressure sensor 700 is performed by applying pressure to one end of a microchannel and leaving the other end open. The channel 507 is the center portion of the microchannel. By varying the applied pressure and at the same time recording the pressure sensor output and flow rate, the capability of the pressure sensor 700 is demonstrated to monitor the local pressure inside the channel. Also, the pressure sensor can function as a flow sensor based on a differential-pressure principle.

Figure 13:
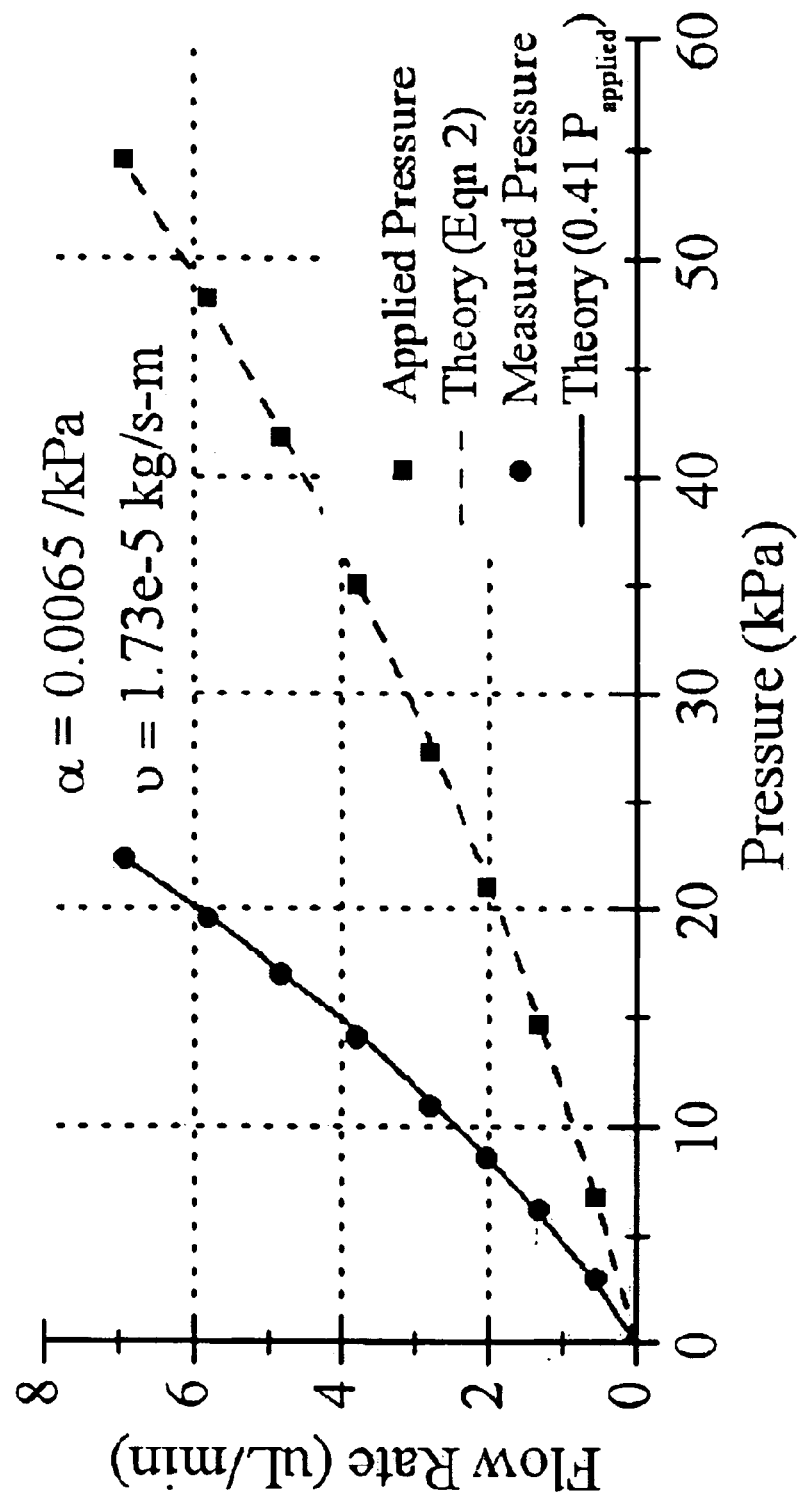
FIGS. 13 and 14 are simplified diagrams showing relationships between flow rate and pressure for a pressure sensor according ton an embodiment of the present invention.
Figure 14:
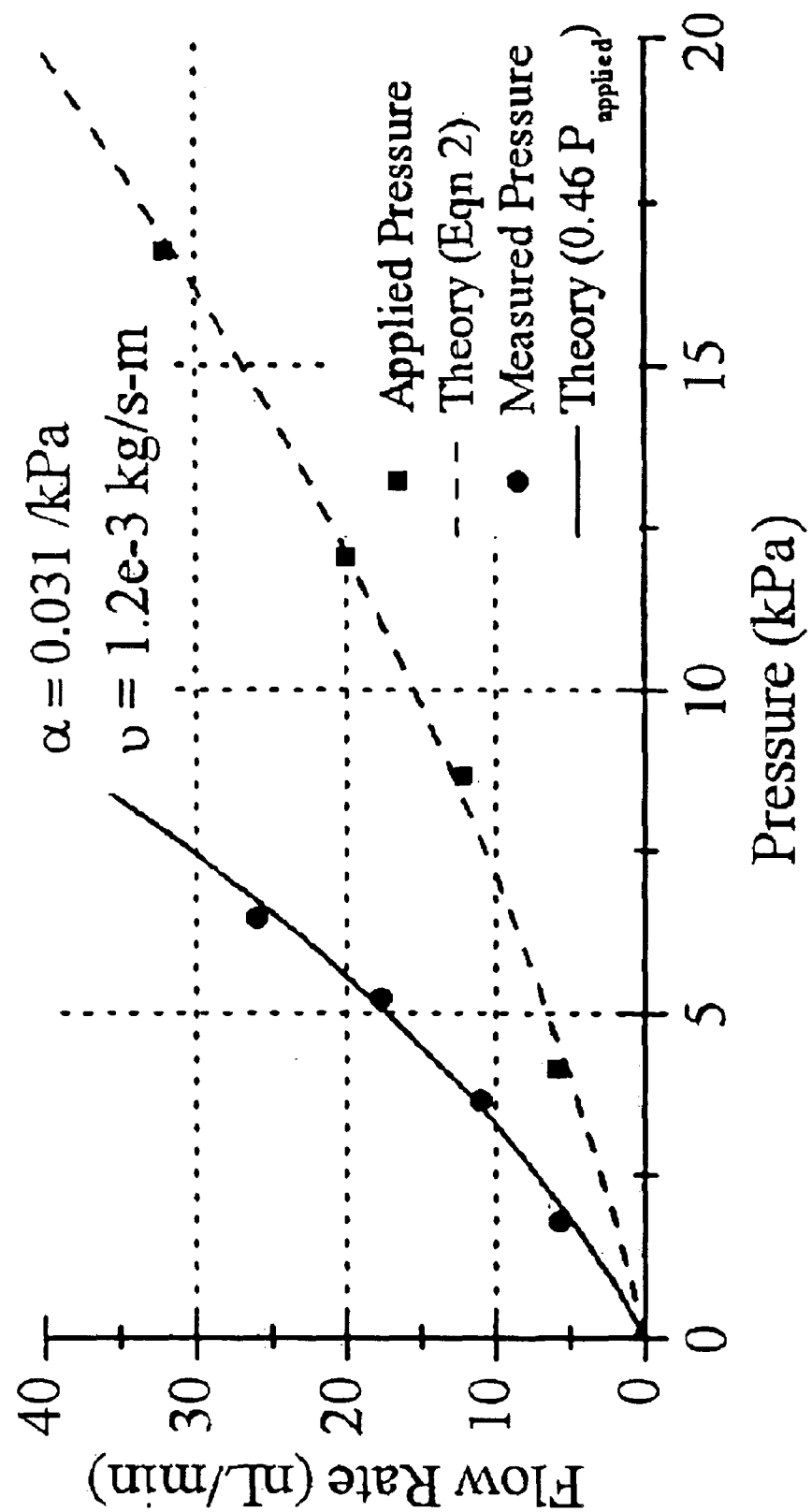

FIGS. 13 and 14 are simplified diagrams showing relationships between flow rate and pressure for the pressure sensor 900 according ton an embodiment of the present invention. These diagrams are merely illustrations, which should not unduly limit the scope of the claims herein. One of ordinary skill in the art would recognize many variations, alternatives, and modifications. For FIG. 13, air is used as the fluid in the channel 503, and for FIG. 14, ethanol is used as the fluid in the channel 503. In each of FIGS. 13 and 14, the applied pressure and the pressure measured by the pressure sensor 900 are illustrated as functions of flow rate. The relation between the flow rate and the applied pressure is fit as follows.

$$Q = \frac{wh_o^3 \Delta P}{12vL}(1 + 2\alpha\Delta P) \quad \text{(Equation 1)}$$

where Q is the flow rate, $\Delta P$ is the applied pressure. L and w are the length and width of the composite membrane respectively. The composite membrane includes the upper electrode 303 and the polymer based layers 301 and 305. v is the viscosity of the fluid in the channel 507. $h_0$ is the height of the microchannel under zero pressure. The term of $(1+2\alpha\Delta P)$ accounts for bulging of the microchannel.

For FIG. 13, v equals about 1.73e-5 kg/s-m for air. By fitting the experimental data, $\alpha$ is found to be 0.0065/kPa. Additionally, the measured pressure in the center of the microchannel is found to be 0.41 of the applied pressure. For FIG. 14, v equals about 1.2e-3 kg/s-m for ethanol. By fitting the experimental data, $\alpha$ is found to be 0.031/kPa. Additionally, the measured pressure in the center of the microchannel is found to be 0.46 of the applied pressure.

According to one embodiment of the present invention, the interdigitated sensor 1000 is calibrated as a volumetric sensor. The volumetric sensor is calibrated by slowly introducing water into the interdigitated sensor 1000. The introduction of the liquid is captured on video and correlated with the capacitance measurements.

Figure 15:
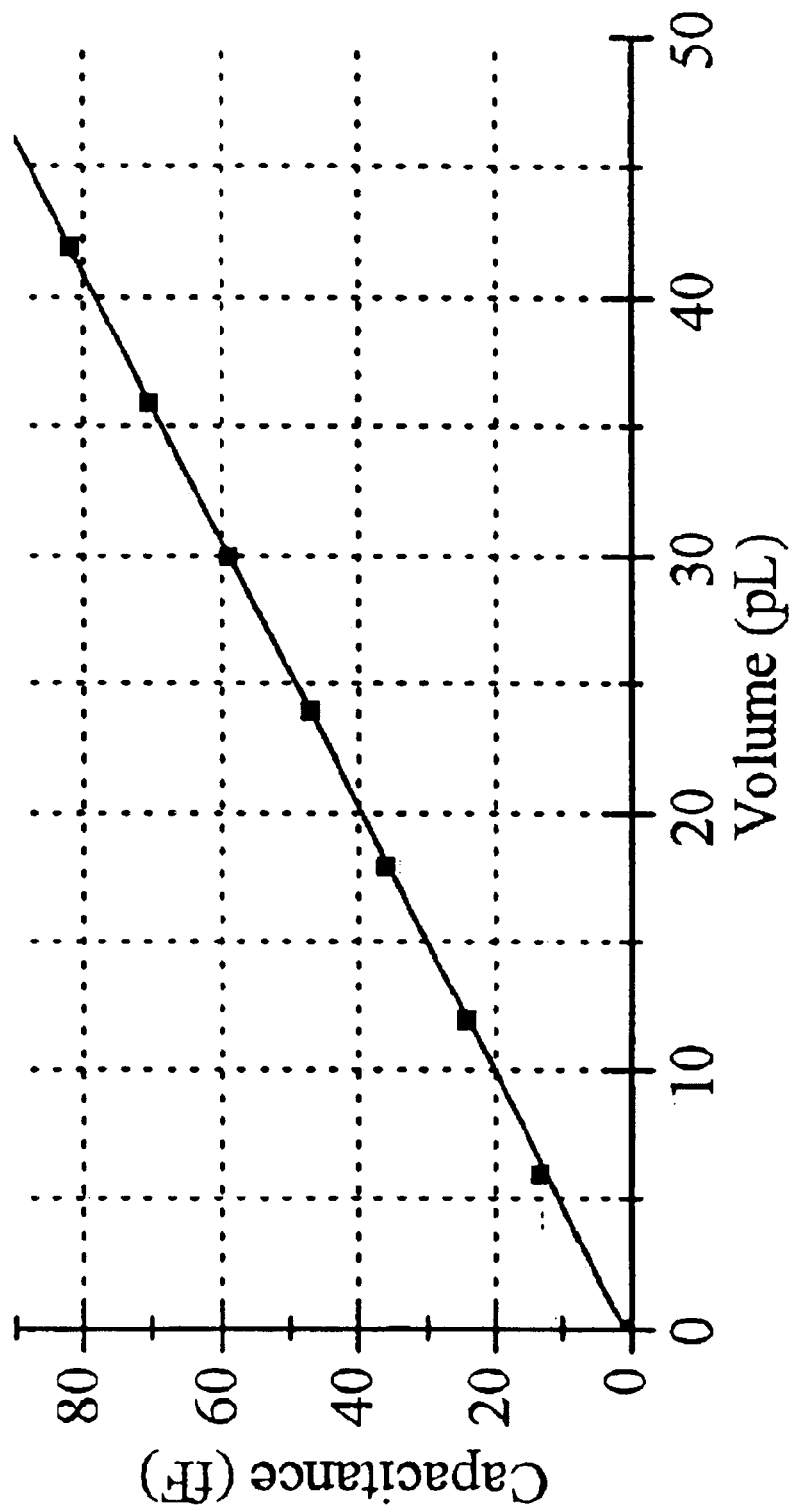
FIG. 15 is a simplified diagram showing relationship between capacitance and volume for an interdigitated sensor according to an embodiment of the present invention.

FIG. 15 is a simplified diagram showing relationship between capacitance and volume for the interdigitated sensor 1000 according to an embodiment of the present invention. This diagram is merely an illustration, which should not unduly limit the scope of the claims herein. One of ordinary skill in the art would recognize many variations, alternatives, and modifications. As shown in FIG. 15, the measurements correspond to the capacitance as the fluid front passes over each successive finger. The cross section of the channel 503 is fixed, so the fluid front position corresponds directly to a volume. For example, the spacing between each finger is 15 $\mu$m which corresponds to 6 pL. The interdigitated sensor 1000 has a volume resolution no larger than 5 pL.

According to one embodiment of the present invention, the parallel plate sensor 900 and the interdigitated sensor 1000 each are used to measure dielectric constant or detect the presence of a fluid in a channel. For example, the capacitance of the parallel plate sensor 900 or the interdigitated sensor 1000 would increase significantly if there is water in the channel 503 as opposed to air. For example, the increase in capacitance for the interdigitated sensor 1000 is measured to be 1.11 pF, and the increase in capacitance for the parallel plate sensor 900 is measured to be 3.38 pF. Additionally, different fluids usually have different dielectric constants, so the parallel plate sensor 900 and the interdigitated sensor 1000 each can distinguish a large variety of fluids, provided their dielectric constants are different.

Figure 16:
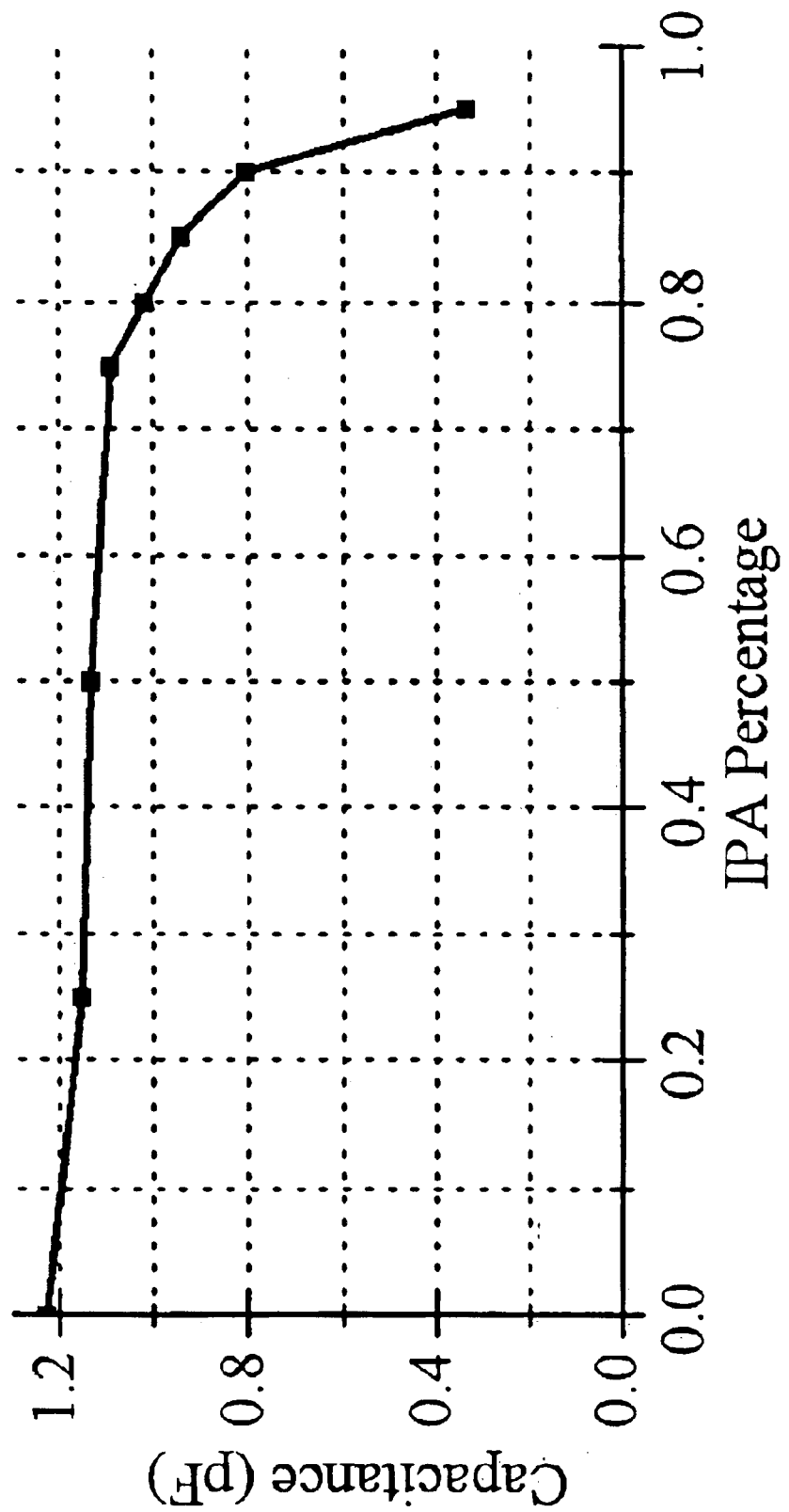
FIG. 16 is a simplified diagram showing relationship between capacitance and mixture for an interdigitated sensor according to an embodiment of the present invention.

Also, the composition of a mixture of liquids can also be determined. The effective dielectric constant is a function of the distribution of the two components as well as the individual dielectric constants. For example, the two liquids mix with predictable distribution. FIG. 16 is a simplified diagram showing relationship between capacitance and mixture for the interdigitated sensor 1000 according to an embodiment of the present invention. This diagram is merely an illustration, which should not unduly limit the scope of the claims herein. One of ordinary skill in the art would recognize many variations, alternatives, and modifications. As shown in FIG. 16, the capacitance is expressed as an increase over an empty channel.

Numerous benefits are achieved using the present invention over conventional techniques depending upon the embodiment. For example, some embodiments of the present invention provide a capacitive sensor with some or all advantages including versatility, flexibility, high sensitivity, small footprints, and easy integration. Certain embodiments of the present invention provide a capacitive sensor suitable for microfluidic applications based on high sensitivity and easy integration. The versatility of the Parylene/photoresist surface micromachining technology facilitates the integration of the sensor with other devices for the creation of an entire microfluidic systems. The sensor provides feedback for controlling the microfluidic system.

It is also understood that the examples and embodiments described herein are for illustrative purposes only, and there can be other variations and alternatives. Various modifications or changes in light of the above description thereof will be suggested to persons skilled in the art and are to be included within the spirit and purview of this application and scope of the appended claims.

What is claimed is:

1. A microfluidic device for capacitive fluidic sensing, the device comprising:
   a fluid channel including an inlet at a first end and an outlet at a second end, the fluid channel being associated with a first polymer based layer and a second polymer based layer;
   a first capacitor electrode coupled to the first polymer based layer;
   a second capacitor electrode coupled to the first polymer based layer and physically separated from the first capacitor electrode;
   an electrical power source coupled between the first capacitor electrode and the second capacitor electrode and causing an electric field at least within the fluid channel;
   wherein the first polymer based layer includes a first polymer;
   wherein the second polymer based layer includes a second polymer.

2. The device of claim 1 wherein each of the first polymer and the second polymer comprises a material selected from a group consisting of Parylene, polyimide, and silicone.

3. The device of claim 2 wherein each of the first polymer and the second polymer comprises Parylene.

4. The device of claim 1, and further comprising:
   a substrate, the first capacitor electrode and the second capacitor electrode being disposed on the substrate.

5. The device of claim 4 wherein the substrate comprises a material selected from silicon and glass.

6. The device of claim 4, and further comprising:
   a layer of silicon oxide, the layer of silicon oxide being disposed between the second capacitor electrode and the substrate.

7. The device of claim 1 wherein the fluid channel contains at least a liquid.

8. The device of claim 1 wherein the fluid channel contains at least a gas.

9. The device of claim 1 wherein each of the first capacitor electrode and the second capacitor electrode comprises a material selected from a group consisting of gold, aluminum, platinum, chrome, titanium, and doped polysilicon.

10. The device of claim 1 wherein the fluid channels is characterized by a channel height ranging from 0.1 to 100 microns.

11. The device of claim 10 wherein the channel height ranges from 1 to 10 microns.

12. The device of claim 1 wherein the fluid channels is characterized by a channel width ranging from 1 to 1000 microns.

13. The device of claim 12 wherein the channel width is equal to 100 microns.

14. The device of claim 1 wherein the first capacitor electrode and the second capacitor electrode are interlocking.

15. The device of claim 1 wherein each of the first polymer layer and the second polymer based layer is characterized by a thickness ranging form 0.1 to 10 microns.

16. The device of claim 1 wherein
   the fluid channel is associated with a fluid volume;
   the fluid volume is associated with a capacitance of a capacitor including the first capacitor electrode, the second capacitor and the fluid channel;
   the capacitance is associated with a volume resolution smaller than 5 pL.

17. The device of claim 1 wherein
   the fluid channel is associated with a fluid;
   the fluid is associated with a capacitance of a capacitor including the first capacitor electrode, the second capacitor and the fluid channel;
   the capacitance is associated with at least a characteristic of the fluid.

18. The device of claim 17 wherein the characteristic of the fluid is a dielectric constant.

19. The device of claim 17 wherein the characteristic of the fluid is a conductivity.

20. The device of claim 17 wherein the fluid comprises a mixture of a plurality of solvents.

21. The device of claim 20 wherein the mixture comprises at least one solvent selected from a group consisting of water, IPA, acetonitrile, acetone, methanol, and ethanol.

22. The device of claim 17 wherein the characteristic of the fluid is a composition of the fluid.

23. The device of claim 1 wherein the first capacitor electrode and the second capacitor electrode are configured as parallel plates.

24. The device of claim 1 wherein
   the first capacitor electrode includes a first plurality of electrode elements;
   the second capacitor electrode includes a second plurality of electrode elements;
   each of the first plurality of electrode elements and the second plurality of electrode elements is associated with a width ranging from 1 to 100 microns.

25. The device of claim 7 wherein
   the first capacitor electrode includes a first electrode element;
   the second capacitor electrode includes a second electrode element;
   the first electrode element is adjacent to the second electrode element;
   the first electrode element is physically separated from the second electrode element by a spacing distance;
   the spacing distance ranges from 1 to 100 microns.

* * * * *

UNITED STATES PATENT AND TRADEMARK OFFICE
CERTIFICATE OF CORRECTION

PATENT NO. : 6,945,116 B2  Page 1 of 1
APPLICATION NO. : 10/802667
DATED : September 20, 2005
INVENTOR(S) : Jun Xie et al.

It is certified that error appears in the above-identified patent and that said Letters Patent is hereby corrected as shown below:

In the Specification:

Column 1, line 15, on the line immediately after "STATEMENT AS TO RIGHTS TO INVENTIONS MADE UNDER FEDERALLY SPONSORED RESEARCH OR DEVELOPMENT", the present paragraph should be deleted and following paragraph should be inserted:

--This invention was made with government support under DARPA/MTO Bioflips Program (Grant No. N66001-00-C-8092); Grant No. 5R01RR06217-10 awarded by the National Institute of Health and Grant No. EEC-9402726 awarded by NSF CNSE Engineering Research Center at Caltech. The government has certain rights in the invention--.

Signed and Sealed this

Sixteenth Day of June, 2009

JOHN DOLL
*Acting Director of the United States Patent and Trademark Office*